United States Patent [19]

Maurer et al.

[11] Patent Number: 5,691,295
[45] Date of Patent: Nov. 25, 1997

[54] DETERGENT COMPOSITIONS

[75] Inventors: Karl-Heinz Maurer, Erkrath; Winfried Pochandke, Monheim; Beatrix Kottwitz; Jorg Poethkow, both of Duesseldorf; Albrecht Weiss, Langenfold; Irmgard Schmidt, Solingen; Horst Upadek, Ratingen, all of Germany

[73] Assignee: Cognis Gesellschaft fuer Biotechnologie mbH, Duesseldorf, Germany

[21] Appl. No.: 373,818

[22] Filed: Jan. 17, 1995

[51] Int. Cl.$^6$ ................................................. C11D 3/386
[52] U.S. Cl. .................. 510/392; 510/292; 510/320; 510/530; 435/219; 435/220; 435/221; 435/222; 435/223; 435/224; 435/225
[58] Field of Search ....................................... 435/219, 220, 435/221, 222, 223, 224, 225; 510/292, 320, 392, 530

[56] References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,703,798 | 3/1955 | Schwartz | 260/211 |
| 3,547,828 | 12/1970 | Mansfield et al. | 252/351 |
| 3,844,959 | 10/1974 | Cracco et al. | 252/8.75 |
| 4,761,249 | 8/1988 | Giede et al. | 252/528 |
| 4,839,075 | 6/1989 | Puchta et al. | 252/8.7 |
| 5,340,735 | 8/1994 | Christianson et al. | 435/221 |
| 5,352,604 | 10/1994 | Wilson et al. | 435/221 |
| 5,500,364 | 3/1996 | Christianson et al. | 435/221 |
| 5,540,850 | 7/1996 | Foster | 510/330 |

FOREIGN PATENT DOCUMENTS

| | | |
|---|---|---|
| 0028865 | 5/1981 | European Pat. Off. |
| 0037026 | 10/1981 | European Pat. Off. |
| 0066944 | 12/1982 | European Pat. Off. |
| 0080223 | 6/1983 | European Pat. Off. |
| 0080748 | 6/1983 | European Pat. Off. |
| 0092355 | 10/1983 | European Pat. Off. |
| 0150386 | 8/1985 | European Pat. Off. |
| 0164514 | 12/1985 | European Pat. Off. |
| 0164552 | 12/1985 | European Pat. Off. |
| 0185427 | 6/1986 | European Pat. Off. |
| 0262588 | 4/1988 | European Pat. Off. |
| 0265832 | 5/1988 | European Pat. Off. |
| 0269977 | 6/1988 | European Pat. Off. |
| 0270974 | 6/1988 | European Pat. Off. |
| 0273125 | 7/1988 | European Pat. Off. |
| 0293753 | 12/1988 | European Pat. Off. |
| 0301298 | 2/1989 | European Pat. Off. |
| 0301414 | 2/1989 | European Pat. Off. |
| 0309931 | 4/1989 | European Pat. Off. |
| 0339550 | 11/1989 | European Pat. Off. |
| 0357969 | 3/1990 | European Pat. Off. |
| 0362671 | 4/1990 | European Pat. Off. |
| 0376705 | 7/1990 | European Pat. Off. |
| 0378261 | 7/1990 | European Pat. Off. |
| 0378262 | 7/1990 | European Pat. Off. |
| 0425427 | 5/1991 | European Pat. Off. |
| 0436835 | 7/1991 | European Pat. Off. |
| 0451921 | 10/1991 | European Pat. Off. |
| 0452428 | 10/1991 | European Pat. Off. |
| 0502325 | 9/1992 | European Pat. Off. |
| 0511456 | 11/1992 | European Pat. Off. |
| 0548599 | 6/1993 | European Pat. Off. |
| 0583536 | 2/1994 | European Pat. Off. |
| 0241984 | 3/1994 | European Pat. Off. |
| 1617141 | 4/1972 | Germany . |
| 2253063 | 5/1973 | Germany . |
| 2412837 | 10/1974 | Germany . |
| 3207847 | 9/1982 | Germany . |
| 3322950 | 1/1984 | Germany . |
| 3436194 | 4/1986 | Germany . |
| 0255884 | 4/1988 | Germany . |
| 3117250 | 12/1991 | Germany . |
| 3207825 | 2/1992 | Germany . |
| 4221381 | 2/1994 | Germany . |
| 4300772 | 7/1994 | Germany . |
| 4238809 | 8/1992 | Japan . |
| 4260610 | 9/1992 | Japan . |
| 9013533 | 11/1990 | WIPO . |
| 9102792 | 3/1991 | WIPO . |
| 9108171 | 6/1991 | WIPO . |
| 9206984 | 4/1992 | WIPO . |
| 9311215 | 6/1993 | WIPO . |
| 9316110 | 8/1993 | WIPO . |

OTHER PUBLICATIONS

Wells et al *PNAS*, vol. 84, pp. 5167–5171, Aug. 1987.
Goddetle et al *J. Mol. Biol*, vol. 228 pp. 580–595 1992.
M. Bahn & R. D. Schmidt, Biotec 1, 119, 1987.
*Proc. Natl. Acad. Sci.*, USA, 84, pp. 5167–5171, Aug. 1987.
*J. Mol. Biol.* (1992) 228, 580–595.
P. Bernfield, S.P. Colowick and N. D. Kaplan, "Methods in Enzymology", vol. 1, 1955, p. 149.
"Detergents and Textile Washing", G. Jacobi & A. Loehr. VCH, Weinheim, ISBN 0–89573–687–X, 1987.
Kraut, *Ann. Rev. Biochem.* 46, 331–358, 1977.
A. Recktenwald et al., *Journal of Biotechnology* 28, 1–23, 1993.
S. Ito et al., *Agric. Biol. Chem.*, 53, (5), 1275–1281, 1989.

*Primary Examiner*—Douglas J. McGinty
*Assistant Examiner*—Kery Fries
*Attorney, Agent, or Firm*—Wayne C. Jaeschke; John E. Drach; Jeffrey S. Steen

[57] ABSTRACT

A laundry detergent for washing fabrics composed of proteinogenic fibers is comprised of at least one surfactant and a proteolytically active amount of a protease having a keratinase/caseinase activity ratio of less than about 0.80.

27 Claims, No Drawings

DETERGENT COMPOSITIONS

BACKGROUND OF THE INVENTION

1. Field of the Invention

This invention relates to detergent compositions containing a protease and combinations of proteases in addition to standard surfactants and which are particularly effective in removing stains and combinations of stains from soiled fabrics such as wool without damaging the fabrics.

2. Description of the Related Art

Enzymes, more particularly proteolytic enzymes, are widely used in laundry detergents, washing aids and cleaning compositions. At present, proteases from the subtilisin family are exclusively used. These are extracellular proteins with a molecular weight in the range from about 20,000 to 45,000. Subtilisins are relatively non-specific enzymes which show esterolytic properties in addition to their hydrolytic effect on peptide bonds. Many representatives of the subtilisins are accurately characterized both physically and chemically. Their three-dimensional structure is often known in detail through X-ray structural analysis. This establishes the prerequisites for molecular modeling and so-called protein engineering in the form of controlled mutagenesis. Genetically engineered modifications of proteases have often been described; thus, 219 protein variants of the subtilisins obtained by protein engineering were known as long ago as June, 1991. Most of these variants were produced to improve the stability of the proteases. For example, an active protease from the subtilisin family which is stable under highly alkaline conditions can be produced in *Bacillus lentus* (DSM 5483), as described in U.S. Pat. No. 5,352,604, the entire contents of which are incorporated herein by reference. This *Bacillus lentus* alkaline protease (BLAP) can be produced by fermentation of the *Bacillus licheniformis* which was transformed with an expression plasmid carrying the gene for BLAP under the control of the promoter from *Bacillus licheniformis* ATCC 53926. Both the composition and the three-dimensional structure of BLAP are known. This protease contains 269 amino acid sequences, a calculated molecular weight of 26,823 Daltons and a theoretical isoelectric point of 9.7. Variants of this *Bacillus lentus* DSM 5483 protease obtainable by mutation are described in U.S. Pat. No. 5,340,735, the entire contents of which are incorporated herein by reference.

The proteases hitherto proposed for use in detergents and washing aids were selected for high proteolytic activity. On account of their low specificity, therefore, fiber damage or fiber destruction by the protease can occur in particular in the event of repeated washing of fabrics of proteinogenic fibers, for example sheet-form textiles of silk or wool. On the other hand, any reduction in protease activity results in a loss of cleaning power noticeable to the user of the detergent. Accordingly, one problem addressed by the present invention was to develop protease-containing detergents which would show reduced activity on proteinogenic fibers, more particularly wool, for substantially the same washing activity. Another problem addressed by the present invention was to develop soil-specific proteases which are proteases that remove specific stains on fabrics such as eggs stains and blood stains and detergent formulations containing such soil-specific proteases.

SUMMARY OF THE INVENTION

One aspect of the present invention relates to detergent compositions for washing fabrics composed of proteinogenic fibers such as wool without causing damage to such fibers. The detergents are comprised of at least one surfactant and a proteolytically active amount of a protease having a keratinase/caseinase activity ratio of less than about 0.80.

Another aspect of the present invention relates to detegent compositions which are particularly effective in removing stains such as blood and egg stains and especially combinations of such stains from fabrics. The detergents are comprised of a combination of proteases which are *Bacillus lentus* DSM 5483 variants and at least one surfactant.

DESCRIPTION OF THE PREFERRED EMBODIMENTS

One aspect of the present invention relates to detergent compositions which contain at least one surfactant and a proteolytically active quantity of a protease having a keratinase/caseinase activity ratio (hereinafter referred to as the KC ratio) of less than about 0.80, preferably less than about 0.70 and more preferably in the range from about 0.2 to about 0.65.

The detergent preferably has a proteolytic activity in the range from about 100 PU/g to around 7500 PU/g.

The present invention also relates to the use of proteases with a KC ratio of less than about 0.80, preferably less than about 0.70 and more preferably in the range from about 0.2 to about 0.65 for washing textiles of proteinogenic fibers or textiles consisting at least partly of proteinogenic fibers.

The KC ratio includes the activity of the protease with respect to two different substrates, casein and keratin.

The proteolytic activity of a protease solution which, in the case of casein as substrate, produces an absorption of 0.500 OD under the described measuring conditions, is defined as 10 PU (protease units) per ml. The cleaning result observed by the user of a protease-containing detergent correlates with this activity expressed in PU. The observed damage to a fabric of proteinogenic fibers correlates with the KC ratio for a constant cleaning result.

As expected in the light of the problem stated above, an only minimal difference in the activities towards casein and keratin was observed in the case of commercial proteases, the KC ratio being relatively close to 1. It was found that proteases with KC ratios of less than 0.80 have to be used to achieve a no longer significantly noticeable degree of damage to proteinogenic fabric.

It has surprisingly been found that proteases having the properties mentioned above can synergistically influence the effect of certain other detergent ingredients and that, conversely, the proteolytic activity of the protease can be synergistically enhanced by certain other detergent ingredients. These effects occur in particular in the case where the surfactant component of the compositions according to the invention contain nonionic surfactants, soil-release copolyesters (more particularly those containing terephthalic acid units), water-insoluble organic builders, water-soluble inorganic and organic builders (more. particularly based on oxidized carbohydrates) and synthetic anionic surfactants of the sulfate and sulfonate type, but not very strongly—if at all—in the case of alkylbenzenesulfonates. Detergents according to the invention preferably contain ingredients of which the properties are enhanced or which enhance the properties of the protease.

The proteases suitable for use in accordance with the invention include genetically engineered variants of *Bacillus lentus* DSM 5483. These variants can be prepared according to the method set forth in US patent application Ser. No. 08/201,120 filed on Feb. 24, 1994, the entire contents of which is incorpated herein by reference and in US patent number 5,340,735. Preferred variants of *Bacillus lentus* DSM 5483 (BLAP) are listed in the following table.

DESCRIPTION OF BLAP MUTANTS

BLAP wild type enzyme
M130 S3T+A188P+V193M+V199I
M131 S3T+V4I+A188P+V193M+V199I
F11 S3T+R99S+A188P+V193M+V199I
F43 S3T+V4I+R99G+A188P+V193M+V199I
F44 S3T+V4I+R99A+A188P+V193M+V199I
F45 S3T+V4I+R99S+A188P+V193M+V199I
F46 S3T+V4I+S154E+A188P+V193M+V199I
F47 S3T+V4I+S154D+A188P+V193M+V199I
F49 S3T+V4I+A188P+V193M+V199I+L211D
F54 S3T+V4I+R99G+A188P'V193M+V199I+L211D
F55 S3T+V4I+S154E+A188P+V193M+V199I+L211D The system used to identify the variants is the same as that used in U.S. Pat. No. 5,340,735 and explained therein. For example, mutant F49is identified as S3T+V4I+A188P+V193M+V199I+L211D. Such a protease is a mutant *Bacillus lentus* DSM 5483 variant wherein the serine residue at position 3 is replaced by threonine, the valine residue at position 4 is replaced by isoleucine, the alanine residue at position 188 is replaced by proline, the valine residue at position 193 is replaced by methionine, the valine residue at position 199 is replaced by isoleucine, and the leucine residue at position 211 is replaced by aspartic acid. The amino acid sequence of the wild-type BLAP protease is set forth as sequence ID number 52 in U.S. Pat. No. 5,340,735.

It has been found that some *Bacillus lentus* DSM 5483 variants showed preferential activity toward blood stains while others showed preferential activity toward egg stains. Mutants that are particularly effective in removing blood and egg stains from fabrics are those mutants made by making the following replacements in the wild-type *Bacillus lentus* DSM 5483 protein: R99G, R99A, R99S, S154D, S154E, L221 D, and L211E. Mutants having replacement amino acid residues at positions 99 and 154 are particularly effective in removing blood stains. Mutants having replacement amino acid residues at position 211 are particularly effective in removing egg stains. It has been found that a combination of mutant enzymes having replacement amino acid residues at positions 99 and 154 and those having replacement amino acid residues at position 211 are particularly effective in removing a combination of blood and egg stains.

Another aspect of the present invention relates to detergent compositions which are particularly effective in removing combinations of stains such as blood and egg stains from fabrics. The detergents are comprised of a combination of proteases which are *Bacillus lentus* DSM 5483 variants and a nonionic surfactant, an anionic surfactant, a soap, or a combination of such surfactants. Protease combinations include any two or more of the *Bacillus lentus* DSM 5483 variants listed in the Table above. A particularly preferred combination is F46+F49 for removing stains comprised of blood and egg stains.

In one preferred embodiment, a detergent according to the invention contains nonionic surfactants selected from fatty alkyl polyglycosides, fatty alkyl polyalkoxylates, more particularly ethoxylates and/or propoxylates, fatty acid polyhydroxyamides and/or ethoxylation and/or propoxylation products of fatty alkylamines, vicinal diols, fatty acid alkyl esters and/or fatty acid amides and mixtures thereof, more particularly in a quantity of 2% by weight to 25% by weight.

In another preferred embodiment, a detergent according to the invention contains synthetic anionic surfactant of the sulfate and/or sulfonate type, more particularly fatty alkyl sulfate, fatty alkyl ether sulfate, sulfofatty acid esters and/or sulfofatty acid disalts, more particularly in a quantity of 2% by weight to 25% by weight. The anionic surfactant is preferably selected from the alkyl or alkenyl sulfates and/or the alkyl or alkenyl ether sulfates in which the alkyl or alkenyl group contains 8 to 22 carbon atoms and, more particularly, 12 to 18 carbon atoms.

In another preferred embodiment, a detergent according to the invention contains water-soluble and/or water-insoluble builders, more particularly selected from alkali metal alumosilicate, crystalline alkali metal silicate with a modulus of >1, monomedc polycarboxylate, polymeric polycarboxylate and mixtures thereof, more particularly in quantities of 2.5% by weight to 60% by weight.

Another, albeit less preferred, embodiment of a detergent according to the invention intended for washing wool or silk fabrics may contain peroxygen-based bleaching agents, more particularly hydrogen peroxide, alkali metal perborate tetrahydrate, alkali metal perborate monohydrate and/or alkali metal percarbonate, more particularly in quantities of 5% by weight to 70% by weight, and optionally bleach activators, more particularly in quantities of 2% by weight to 10% by weight.

Finally, another embodiment of a detergent according to the invention contains soil-release agents based on copolyesters of dicarboxylic acids and glycols which may be present in particular in quantities of 0.01% by weight to 5% by weight. These soil-release agents, which are particularly effective by virtue of their chemical similarity to polyester fibers, but are also capable of developing the required effect in fabrics of other materials are copolyesters containing dicarboxylic acid units, alkylene glycol units and polyalkylene glycol units. Soil-release copolyesters of the type mentioned and their use in detergents have been known for some time.

The detergent compositions according to the invention contain at least one surfactant which includes soaps. The surfactants can be nonionic or anionic surfactants or a combination of nonionic and anionic suffactants or a combination of nonionic and anionic surfactants and one or more soaps.

Suitable nonionic surfactants include the alkoxylates, more particularly ethoxylates and/or propoxylates, of saturated or mono- to polyunsaturated linear or branched alcohols containing 10 to 22 carbon atoms and preferably 12 to 18 carbon atoms. The degree of alkoxylation of the alcohols is generally between 1 and 20 and preferably between 3 and 10. They may be obtained in known manner by reaction of the corresponding alcohols with the corresponding alkylene oxides. Derivatives of the fatty alcohols are particularly suitable, although their branched-chain isomers, more particularly so-called oxoalcohols, may also be used for the production of useful alkoxylates. Accordingly, the alkoxylates, more particularly ethoxylates, of primary alcohols containing linear groups, more particularly dodecyl, tetradecyl, hexadecyl or octadecyl groups, and mixtures thereof may be used. In addition, corresponding alkoxylation products of alkylamines, vicinal diols and carboxylic acid amides corresponding to the above-mentioned alcohols in regard to the alkyl moiety are also suitable. Alkyl polyglycosides suitable for incorporation in the detergents according to the invention are compounds corresponding to the general formula $(G)_n$—$OR^1$, where $R^1$ is an alkyl or alkenyl radical containing 8 to 22 carbon atoms, G is a glycose unit and n is a number of 1 to 10. The glycoside component $(G)_n$ is an oligomer or polymer of naturally occurring aldose or ketose monomers, including in particular glucose, mannose, fructose, galactose, talose, gulose, altrose, allose, idose, ribose, arabinose, xylose and lyxose. The oligomers consisting of such glucoside-bonded monomers are characterized not only by the type of sugars present in them, but also by their number, the so-called degree of oligomerization. As an analytically determined quantity, the degree of oligomerization n is generally a broken number which may assume a value of 1 to 10 and, in the case of the glycosides preferably used, a value below 1.5 and, more particularly, between 1.2 and 1.4. Glucose is the preferred monomer unit by virtue of its ready availability. The alkyl or alkenyl substituent $R^1$ of the glycosides also preferably emanates from readily accessible derivatives of renewable raw materials, more particularly from fatty alcohols, although branched-chain isomers thereof, more particularly so-called oxoalcohols, may also be used for the production of useful glycosides. Accordingly, primary alcohols with linear octyl, decyl, dodecyl, tetradecyl, hexadecyl or octadecyl groups and mixtures thereof are particularly suitable. Particularly preferred alkyl glycosides contain a cocofatty alkyl group, i.e. mixtures in which—essentially—$R^1$ is dodecyl and $R^1$ is tetradecyl.

The nonionic surfactant is preferably present in the detergents according to the invention in quantities of 1% by weight to 30% by weight and more preferably in quantities of 1% by weight to 25% by weight.

In addition to or instead of the nonionic surfactant, the detergents according to the invention may contain other surfactants, preferably synthetic anionic surfactants of the sulfate or sulfonate type, in quantities of preferably not more than 20% by weight and, more preferably, in quantities of 0.1% by weight to 18% by weight, based on the detergent as a whole. Synthetic anionic surfactants particularly suitable for use in the detergents according to the invention are the alkyl and/or alkenyl sulfates containing 8 to 22 carbon atoms which contain an alkali metal, ammonium or alkyl- or hydroxyalkyl-substituted ammonium ion as counterion. Derivatives of fatty alcohols containing 12 to 18 carbon atoms and branched-chain analogs thereof, so-called oxoalcohols, are preferred. The alkyl and alkenyl sulfates may be prepared in known manner by reaction of the corresponding alcohol component with a typical sulfating agent, more particularly sulfur trioxide or chlorosulfonic acid, and subsequent neutralization with alkali metal, ammonium or alkyl- or hydroxyalkyl-substituted ammonium bases. Alkyl and/or alkenyl sulfates such as these are preferably present in the detergents according to the invention in quantities of 0.1% by weight to 20% by weight and more preferably in quantities of 0.5% by weight to 18% by weight.

Suitable surfactants of the sulfate type also include the sulfated alkoxylation products of the alcohols mentioned, so-called ether sulfates. These ether sulfates preferably contain 2 to 30 and, more particularly, 4 to 10 ethylene glycol groups per molecule. Suitable anionic surfactants of the sulfonate type include the α-sulfoesters obtainable by reaction of fatty acid esters with sulfur trioxide and subsequent neutralization, more particularly the sulfonation products derived from $C_{8-22}$ and preferably $C_{12-18}$ fatty acids and $C_{1-6}$ and preferably $C_{1-4}$ linear alcohols, and the sulfofatty acids emanating from these sulfonation products through formal saponification.

Other optional surface-active ingredients include soaps, suitable soaps being saturated fatty acid soaps, such as the salts of lauric acid, myristic acid, palmitic acid or stearic acid, and soaps derived from natural fatty acid mixtures, for example coconut oil, palm kernel oil or tallow fatty acids. Soap mixtures of which 50% by weight to 100% by weight consist of saturated $C_{12-18}$ fatty acid soaps and up to 50% by weight of oleic acid soap are particularly preferred. Soap is preferably present in quantities of 0.1% by weight to 5% by weight. However, larger quantities of soap of up to 20% by weight may be present in particular in liquid detergents.

A detergent according to the invention preferably contains 20% by weight to 55% by weight of water-soluble and/or water-insoluble, organic and/or inorganic builders. Water-soluble organic builders include, in particular, those from the class of polycarboxylic acids, more particularly citric acid and sugar acids, and the class of polymeric (poly)carboxylic acids, more particularly the polycarboxylates obtainable by oxidation of polysaccharides, polymeric acrylic acids, methacrylic acids, maleic acids and copolymers thereof which may even contain small amounts of polymerizable substances with no carboxylic acid functionality in copolymerized form. The relative molecular weight of the homopolymers of unsaturated carboxylic acids is generally in the range from 5,000 to 200,000 while the relative molecular weight of the copolymers is in the range from 2,000 to 200,000 and preferably in the range from 50,000 to 120,000, based on free acid. A particularly preferred acrylic acid/maleic acid copolymer has a relative molecular weight of 50,000 to 100,000. Suitable, but less preferred compounds of this class are copolymers of acrylic acid or methacrylic acid with vinyl ethers, such as vinylmethyl ethers, vinyl esters, ethylene, propylene and styrene, in which the acid makes up at least 50% by weight. Other suitable water-soluble organic builders are terpolymers containing two carboxylic acids and/or salts thereof as monomers and vinyl alcohol and/or a vinyl alcohol derivative or a carbohydrate as the third monomer. The first acidic monomer or its salt is derived from a monoethylenically unsaturated ($C_{3-8}$ carboxylic acid and preferably from a $C_{3-4}$ monocarboxylic acid, more particularly from (meth)acrylic acid. The second acidic monomer or its salt may be a derivative of a $C_{4-8}$ dicarboxylic acid, preferably a $C_{4-8}$ dicarboxylic acid, maleic acid being particularly preferred. In this case, the third monomer unit is formed by vinyl alcohol and/or preferably by an esterified vinyl alcohol. Vinyl alcohol derivatives in the form of an ester of short-chain carboxylic acids, preferably $C_{1-4}$ carboxylic acids, with vinyl alcohol are particularly preferred. Preferred terpolymers contain 60% by weight to 95% by weight and, more particularly, 70% by weight to 90% by weight of (meth)acrylic acid or (meth)acrylate, more preferably acrylic acid or acrylate, and maleic acid or maleate and 5% by weight to 40% by weight and preferably 10% by weight to 30% by weight of vinyl alcohol and/or vinyl acetate. Terpolymers in which the ratio by weight of (meth)acrylic acid or (meth)acrylate to maleic acid or maleate is between 1:1 and 4:1, preferably between 2:1 and 3:1 and more preferably between 2:1 and 2.5:1 are most particularly preferred (both the quantities and the ratios by weight being based on the acids). The second acidic monomer or its salt may even be a derivative of an allyl sulfonic acid substituted in the 2-position by an alkyl radical, preferably by a $C_{1-4}$ alkyl radical, or by an aromatic radical preferably derived from benzene or benzene derivatives. Preferred terpolymers contain 40% by weight to 60% by weight and more particularly 45% by weight to 55% by weight of (meth)acrylic acid or (meth)acrylate, more preferably acrylic acid or acrylate, 10% by weight to 30% by weight and preferably 15% by weight to 25% by weight of methallyl sulfonic acid or methallyl sulfonate and, as the third monomer, 15% by weight to 40% by weight and preferably 20% by weight to 40% by weight of a carbohydrate. This carbohydrate may be, for example, a mono-, di-, oligo- or polysaccharide, mono-, di- or oligosaccharides being preferred, sucrose being particularly preferred. Weak points responsible for the ready biodegradability of the polymer are presumably incorporated therein through the use of the third monomer. These terpolymers generally have a relative molecular weight in the range from 1,000 to 200,000, preferably in the range from 200 to 50,000 and more preferably in the range from 3,000 to 10,000. They may be used in the form of aqueous solutions, preferably 30 to 50% by weight aqueous solutions, particularly for the production of liquid detergents. All the polycarboxylic acids mentioned are generally used in the form of their water-soluble salts, more particularly their alkali metal salts.

Organic builders of the type in question are preferably present in quantities of up to 40% by weight, more preferably in quantities of up to 25% by weight and most preferably in quantities of 1% by weight to 5% by weight. Quantities near the upper limit mentioned are preferably used in paste-form or liquid, more particularly water-containing, detergents according to the invention.

Crystalline or amorphous alkali metal alumosilicates in particular are used as the water-insoluble, water-dispersible inorganic builders in quantities of up to 50% by weight and preferably in quantities of not more than 40% by weight and, in liquid detergents, in quantities of 1% by weight to 5% by weight. Among these alumosilicates, crystalline sodium alumosilicates in detergent quality, more particularly zeolite A, P and optionally X, are preferred. Quantities near the upper limit mentioned are preferably used in solid particulate detergents. Suitable alumosilicates contain no particles larger than 30 μm in size, at least 80% by weight consisting of particles below 10 pm in size. Their calcium binding capacity is generally in the range from 100 to 200 mg CaO per gram.

Suitable substitutes or partial substitutes for the alumosilicate mentioned are crystalline alkali metal silicates which may be present either on their own or in admixture with amorphous silicates. The alkali metal silicates suitable for use as builders in the detergents according to the invention preferably have a molar ratio of alkali metal oxide to $SiO_2$ of less than 0.95 and, more particularly, in the range from 1:1.1 to 1:12 and may be present in amorphous or crystalline form. Preferred alkali metal silicates are the sodium silicates, more particularly amorphous sodium silicates, with a molar ratio of $Na_2O$ to $SiO_2$ of 1:2 to 1:2.8. Amorphous alkali metal silicates such as these are commercially available, for example, as PORTIL®. Those with a molar ratio of $Na_2O$ to $SiO_2$ of 1:1.9 to 1:2.8 are preferably used in solid form and not in the form of a solution in the production of detergents according to the invention. Preferred crystalline silicates, which may be present either on their own or in admixture with amorphous silicates, are crystalline layer silicates with the general formula $Na_2Si_xO_{2x+1} \cdot yH_2O$, in which x—the so-called modulus—is a number of 1.9 to 4 and y is a number of 0 to 20, preferred values for x being 2, 3 or 4. Preferred crystalline layer silicates are those in which x in the general formula assumes the value 2 or 3. Both β- and δ-sodium disilicates ($Na_2Si_2O_5 \cdot yH_2O$) are particularly preferred. δ-Sodium silicates with a modulus of 1.9 to 3.2 are preferred. Substantially water-free crystalline alkali metal silicates corresponding to the above general formula, in which x is a number of 1.9 to 2.1 may also be used in detergents according to the invention. Another preferred embodiment of detergents according to the invention are crystalline sodium layer silicate having a modulus of 2 to 3. Crystalline sodium silicates with a modulus of 1.9 to 3.5 are used in another preferred embodiment of detergents according to the invention. The alkali metal silicate content of the detergents according to the invention is preferably 1% by weight to 50% by weight and more preferably 5% by weight to 35% by weight, based on anhydrous active substance. If an alkali metal alumosilicate, more particularly zeolite, is also present as an additional builder, the alkali metal silicate content is preferably 1% by weight to 15% by weight and more preferably 2% by weight to 8% by weight, based on anhydrous active substance. In that case, the ratio by weight of alumosilicate to silicate, based on anhydrous active substances, is preferably 4:1 to 10:1. In detergents containing both amorphous and crystalline alkali metal silicates, the ratio by weight of amorphous alkali metal silicate to crystalline alkali metal silicate is preferably 1:2 to 2:1 and more preferably 1:1 to 2:1.

In addition to the inorganic builder mentioned, other water-soluble or water-insoluble inorganic substances may be used in the detergents according to the invention. Alkali metal carbonates, alkali metal hydrogen carbonates and alkali metal sulfates and mixtures thereof are suitable in this regard. The additional inorganic material may be present in quantities of up to 70% by weight, but is preferably absent altogether.

To adjust an optionally acidic or mildly alkaline pH value of, in particular, about 8.0 to 9.5 in a 1% by weight aqueous solution, the detergents according to the invention may contain solid inorganic and/or organic acids or acidic salts, for example alkali metal hydrogen sulfates, succinic acid, adipic acid or glutaric acid and mixtures thereof. Acidic substances such as these are preferably present in the detergents according to the invention in quantities of not more than 5% by weight and, more particularly, in quantities of 0.1% by weight to 3% by weight.

The detergents according to the invention may additionally contain other typical detergent ingredients. These optional ingredients include, in particular, complexing agents for heavy metals, for example aminopolycarboxylic acids, aminohydroxypolycarboxylic acids, polyphosphonic acids and/or aminopolyphosphonic acids, redeposition inhibitors, for example cellulose ethers, dye transfer inhibitors, for example polyvinyl pyrrolidones, foam inhibitors, for example organopolysiloxanes or paraffins, solvents and optical brighteners, for example stilbene disulfonic acid derivatives. The detergents according to the invention preferably contain up to 1% by weight and, more particularly, 0.01% by weight to 0.5% by weight of optical brighteners, more particularly compounds from the class of substituted 4,4'-bis-(2,4,6-triamino-s-triazinyl)-stilbene-2, 2'-disulfonic acids, up to 5% by weight and, more particularly, 0.1% by weight to 2% by weight of complexing agents for heavy metals, more particularly aminoalkylene phosphonic acids and salts thereof, up to 3% by weight and, more particularly, 0.5% by weight to 2% by weight of deposition inhibitors and up to 2% by weight and, more particularly, 0.1% by weight to 1% by weight of foam inhibitors, the percentages by weight mentioned being based on the detergent as a whole.

Besides water, solvents which are used in particular in liquid detergents according to the invention are preferably water-miscible solvents, including lower alcohols, for example ethanol, propanol, isopropanol and isomeric butanols, glycerol, lower glycols, for example ethylene and propylene glycol, and the ethers derived from the classes of compounds mentioned.

The typical enzyme stabilizers optionally present, more particularly in liquid detergents according to the invention, inclOde aminoalcohols, for example mono-, di-, triethanolamine and propanolamine and mixtures thereof, the lower carboxylic acids, boric acid or alkali metal borates, and boric acid/carboxylic acid combinations.

Suitable foam inhibitors include long-chain soaps, more particularly behenic soap, fatty acid amides, paraffins, waxes, microcrystalline waxes, organopolysiloxanes and mixtures thereof which, in addition, may contain microfine, optionally silanized or otherwise hydrophobicized silica. For use in particulate detergents according to the invention, foam inhibitors such as these are preferably deposited on granular water-soluble supports.

In addition, the detergent according to the invention may contain redeposition inhibitors. The function of redeposition inhibitors is to keep the soil detached from the fibers suspended in the liquor and thus to prevent discoloration of the fibers. Suitable redeposition inhibitors are water-soluble, generally organic colloids, for example the water-soluble salts of polymeric carboxylic acids, glue, gelatine, salts of ether carboxylic acids or ether sulfonic acids or starch or cellulose or salts of acidic sulfuric acid esters of cellulose or starch. Water-soluble polyamides containing acidic groups are also suitable for this purpose. Soluble starch preparations and other starch products than those mentioned above, for example partly hydrolyzed starch, may also be used. Sodium carboxymethyl cellulose, methyl cellulose, methyl hydroxyethyl cellulose and mixtures thereof are preferably used.

The bleaching agents which may be used as further ingredients of detergents according to the invention are the per compounds generally used in detergents, such as perborate which may be present as tetrahydrate or monohydrate, percarbonate, perpyrophosphate and persilicate which are generally present in the form of alkali metal salts, more particularly sodium salts. Bleaching agents such as these are preferably present in detergents according to the invention in quantities of up to 25% by weight, more preferably in quantities of up to 15% by weight and most preferably in quantities of 5% by weight to 15% by weight, based on the detergent as a whole.

The bleach activators present as an optional component include the N-acyl or O-acyl compounds typically used, for example polyacylated alkylenediamines, more particularly tetraacetyl ethylenediamine, acylated glycolurils, more particularly tetraacetyl glycoluril, N-acylated hydantoins, hydrazides, triazoles, urazoles, diketopiperazines, sulfurylamides and cyanurates, also carboxylic anhydrides, more particularly phthalic anhydride, carboxylic acid esters, more particularly sodium isononanoyl phenol sulfonate, and acylated sugar derivatives, more particularly pentaacetyl glucose. To avoid interaction with the per compounds during storage, the bleach activators may have been coated with shell-forming substances or granulated in known manner, tetraacetyl ethylenediamine granulated with carboxymethyl cellulose with average particle sizes of 0.01 mm to 0.8 mm, and/or granulated 1,5-diacetyl-2,4-dioxohexahydro-1,3,5-triazine, being particularly preferred. The bleach activators are preferably present in detergents according to the invention in quantities of up to 8% by weight and more particularly in quantities of 2% by weight to 6% by weight, based on the detergent as a whole.

Enzymes optionally present in addition to protease include, in particular, enzymes from the class of lipases, cutinases, amylases, cellulases, pullulanases, oxidases and peroxidases and mixtures thereof. Enzymes obtained from fungi or bacterial strains are preferably used.

The amylases suitable for use in detergents according to the invention include the enzymes obtainable from bacteria or fungi which have a pH optimum preferably in the alkaline range up to about pH 10. Useful commercial products are, for example, TERMAMYL® and MAXAMYL®. Amylase is preferably used in the detergent according to the invention in such quantities that the final detergent contains 0.01 KNU/g to 2 KNU/g ("Kilo Novo Units" per gram according to the standard method of the Novo Company, 1 KNU being the quantity of enzyme which degrades 5.26 kg of starch at pH 5.6/37° C. as determined by the method described by Methods in Enzymology, Vol. 1, 1955, page 149), preferably 0.015 KNU/g to 1.8 KNU/g and more preferably 0.03 KNU/g to 1.6 KNU/g.

The cellulase suitable for use in accordance with the invention also belongs to the enzymes obtainable from bacteria or fungi which have a pH optimum preferably in the almost neutral to mildly alkaline pH range from 6 to 9.5. They are preferably used in the detergent according to the invention in such quantities that the final detergent has a cellulolytic activity of 0.05 IU/g to 1.5 IU/g ("International Units" per gram, based on the enzymatic hydrolysis of Na carboxymethyl cellulose at pH 9.0/40° C., preferably 0.07 IU/g to 1.4 IU/g and more preferably 0.1 IU/g to 1.3 IU/g. Suitable commercial products are, for example, CELLUZYME®, a product of Novo Nordisk, or KAC®, a product of Kao.

The enzymes may be adsorbed in known manner onto supports, encapsulated in shell-forming substances and/or granulated in conjunction with support substances to make then easier to handle and to protect them against premature inactivation if they are to be incorporated in particulate detergents. The enzymes optionally present in addition to protease are preferably present in detergents according to the invention in quantities of up to 2% by weight and more preferably in quantities of 0.01% by weight to 1.5% by weight, based on the detergent as a whole.

In one preferred embodiment, a detergent according to the invention is particulate and contains 20% by weight to 55% by weight of inorganic builder, up to 15% by weight and more particularly from 2% by weight to 12% by weight of water-soluble organic builder, 2.5% by weight to 20% by weight of synthetic anionic surfactant, 1% by weight to 20% by weight of nonionic surfactant, up to 25% by weight and, more particularly, from 1% by weight to 15% by weight of bleaching agent, up to 8% by weight and, more particularly, from 0.5% by weight to 6% by weight of bleach activator and up to 20% by weight and, more particularly, from 0.1% by weight to 15% by weight of inorganic salts, more particularly alkali metal carbonate and/or sulfate, and up to 2% by weight and, more particularly, from 0.4% by weight to 1.2% by weight of particulate enzymes besides protease, more particularly lipase, cutinase, amylase, cellulase, pullulanase, oxidase and/or peroxidase.

In another preferred embodiment, a powder-form detergent according to the invention intended in particular for use as a light-duty detergent contains 20% by weight to 55% by weight of inorganic builders, up to 15% by weight and, more particularly, from 2% by weight to 12% by weight of water-soluble organic builders, from 4% by weight to 24% by weight of nonionic surfactant, up to 15% by weight and, more particularly, from 1% by weight to 10% by weight of synthetic anionic surfactant, up to 65% by weight and, more particularly, from 1% by weight to 30% by weight of inorganic salts, more particularly alkali metal carbonate and/or sulfate, and neither bleaching agents nor bleach activators.

Another preferred embodiment of the detergent according to the invention is a liquid detergent containing 5% by weight to 35% by weight of water-soluble organic builders, up to 15% by weight and, more particularly, from 0.1% by weight to 5% by weight of water-insoluble inorganic builders, up to 15% by weight and, more particularly, from 0.5% by weight to 10% by weight of synthetic anionic surfactant, from 1% by weight to 25% by weight of nonionic surfactant, up to 15% by weight and, more particularly, from 4% by weight to 12% by weight of soap and up to 30% by weight and, more particularly, from 1% by weight to 25% by weight of water and/or water-miscible solvent and also up to 10% by weight and, more particularly, from 0.01% by weight to 7.5% by weight of an enzyme stabilizing system. The protease in each of the above preferred embodiments is variant F49 having the amino acid substitutions S3T+V41+A188P+V193M+V1991+L211D.

Particulate detergents according to the invention may be produced very easily by mixing the individual particles in a standard mixer, more particularly a drum mixer, roller mixer, ribbon mixer or free-fall mixer, other optional powder-form components and, if desired, even liquid or liquefied components, including in particular nonionic surfactants, but also dyes and fragrances, optionally being incorporated by spraying. The components capable of withstanding high temperatures are preferably converted into a powder-form product in known manner by spray drying of an aqueous slurry and the powder obtained is mixed with protease and, optionally, other enzymatic substances and other heat-sensitive components, including in particular bleaching agents. The incorporation of individual constituents by mixing in granules or an extrudate containing them is also possible and is particularly preferred for the production of detergents according to the invention with high apparent densities of, preferably, 650 g/l to 900 g/l. Flowable or liquid detergents according to the invention may be produced simply by mixing the ingredients or compounds thereof which may be present in liquid form or in the form of a solution in water or a given solvent.

The following examples are meant to illustrate but not to limit the invention.

EXAMPLE 1

Measurement of the KC Ratio

The KC ratio of protease F49 and, for comparison, the KC ratios of three commercial proteases were determined by the method described above. The following results were obtained:

| Protease | KC ratio |
|---|---|
| MAXACAL ® [a] | 0.92 |
| SAVINASE ® [b] | 0.80 |
| BLAP ® | 0.83 |
| F49 | 0.63 |

[a]Manufacturer: Gist Brocades, Netherlands
[b]Manufacturer: Novo Nordisk, Denmark

EXAMPLE 2

Determination of Damage to Wool 1 g of wool yarn was added to 50 ml of an F 49-containing sodium carbonate buffer solution (pH 10.5) with a proteolytic activity of 5.6 PU/ml and the whole was left to react for 1 hour at room temperature. The quantity of amino acids released and peptides was then determined with TNBS (control determination in buffer solution without protease). The wool damage value obtained under these conditions for the protease BLAP was put at 100%. Under these conditions, the protease F 49 had a value of 31%.

EXAMPLE 3

Determination of Damaged Silk

The test described in Example 2 was repeated using 1 g of silk yarn. The following silk damage values were obtained:

| Protease | Silk damage |
|---|---|
| BLAP | 100% |
| ESPERASE ®[a] | 165% |
| SAVINASE ®[a] | 89% |
| F49 | 28% |

[a]Manufacturer: Novo Nordisk, Denmark

EXAMPLE 4

Determination of Wool Damage (40° C.)

In a MIELE® Electronic W 793 washing machine, articles of clothing of wool were washed 9 times at 40° C. (water hardness 16° d, liquor ratio 1:15) in the presence of ballast washing of cotton (total load 1.2 kg). 98 g of an enzyme-free coloreds detergent (control test), to which 49 ml of a BLAP 140 solution (comparison test) or an equally active quantity, expressed in PU of F 49 (invention) had been added, were used in the wash liquor. The washed woollen fabrics were dried and pieces of specific dimensions were cut out and weighed. The reduction in weight, expressed in % of the value before washing, is shown in the following Table:

| Woollen fabric | Invention | Comparison |
|---|---|---|
| KUNERT ® darkgrey | 0.19% | 3.76% |
| FALKE ® bristol 100 brown | 7.80% | 37.15% |
| FALKE ® bristol dark red[a] | 4.50% | 16.99% |
| LIBEE ® light brown | 3.26 | 23.13% |

[a]Blend of 80% Merino wool and 20% polyamide

EXAMPLE 5

Determination of Wool Damage (60° C.)

Example 4 was repeated using grey socks of pure wool, the proteases again being used in quantities of equal activity (1080 PU/g of the detergent); in contrast to Example 4, 5 washes were carried out at 60° C. The reduction in weight was only 10.7% where the protease F 49 was used and 40.5% where BLAP® was used.

EXAMPLE 6

Determination of Proteolytic Activity

A solution containing 12 g/l of the substrate (casein or keratin) and 30 mM of sodium tripolyphosphate in water with a hardness of 15° dH (containing 0.058% by weight of $CaCl_2.2H_2O$, 0.028% by weight of $MgCl_2.6H_2O$ and 0.042% by weight of $NaHCO_3$) is heated to 70° C. and the pH is adjusted to a value of 8.5 by addition of 0.1 N NaOH at 50° C. 200 µl of a solution of the enzyme to be tested in 2% by weight sodium tripolyphosphate buffer solution (pH 8.5) are added to 600 μl of the substrate solution. The reaction mixture is incubated for 15 minutes at 50° C. The reaction is then terminated by addition of 500 μl of TCA solution (0.44M trichloroacetic acid and 0.22M sodium acetate in 3% by volume acetic acid) and cooling (ice bath at 0° C., 15 minutes). The protein insoluble in TCA is removed by centrifugation and 900 μl of the supernatant phase are diluted with 300 μl of 2 N NaOH. The absorption of this solution at 290 nm is determined with an absorption spectrometer, the absorption zero value having to be determined by measurement of a centrifuged solution prepared by mixing 600 μl of the above-mentioned TCA solution with 600 μl of the above-mentioned substrate solution and subsequent addition of the enzyme solution.

EXAMPLE 7

Washing Performance

Pre-washed cotton fabrics were soiled with equal amounts of soil and air dried for 3 days. Launderometer beakers were filled with 6 swatches of soiled and unsoiled cotton and 10 metal balls (1 cm in diameter) and washed in an Atlas LP-2 type laundrometer for 30 minutes with a final temperature of 30° C., which was reached after 4 minutes of heating. A fine specialty detergent formulation was used for easy-care and colored fabrics (0.75 g/100 ml). A heavy duty compact detergent (0.5 g/100 ml) and a super compact detergent concentrate (0.4 g/100 ml) were also used. The composition of the detergents is described in "Detergents and Textile Washing", G. Jacobi & A. Löhr, VCH, Weinheim, ISBN 0-89573-687-X, 1987. The water used was 16° dH (German Hardness) and the pH was 4. Enzyme activities of the detergents were 0, 50, 100, 200, 300, 400, 500, 700, and 1000 HPE/g detergent. After washing, the test swatches were rinsed in tap water, air dried, and ironed. The enzymatic washing effect was determined by the change (ΔRem) in the remission (%Rem) at 440 nm measured using a Dr. Lange color difference measuring instrument Micro Color, ΔRem being the difference in remission after wash with protease added and the remission after wash without protease. The results of washing performance for various enzyme-containing detergents and detergent compositions containing a combination of enzymes are given in Tables 2 and 3 below. Each entry is a ratio of the amount of mutant enzyme achieving a standard ΔRem, versus the amount of the wild-type enzyme to achieve an identical cleaning effect. A entry of 2 indicates that twice as much of the wild-type enzyme was needed as a particular mutant to achieve the same cleaning effect. The data also show that a detergent composition containing a combination of mutants F46 and F49 produced a greater cleaning effect than the average of the individual enzymes.

TABLE 2

Washing Effect of Enzymes on Blood-Milk-Soot Stains

| Enzyme | Detergent | |
|---|---|---|
|  | Heavy Duty | Heavy Duty Compact |
| BLAP/M131 | 1 | 1 |
| F46 | 2.9 | 1.9 |
| F49 | 1.8 | 1.0 |
| F46 + F49 | 2.6 | 2.2 |

TABLE 3

Washing Effect of Enzymes on Egg-Soot Stains

| Enzyme | Detergent | |
|---|---|---|
|  | Heavy Duty | Heavy Duty Compact |
| BLAP/M131 | 1 | 1 |
| F46 | 1.5 | 1.3 |
| F49 | 4.0 | 1.7 |
| F46 + F49 | 3.3 | 2.2 |

What is claimed is:

1. A detergent composition for washing fabrics composed of proteinogenic fibers comprising at least one surfactant and a proteolytically active amount of a *Bacillus lentus* protease selected from the group consisting of F49 variant having S3T+V4I+A188P+V193M+V199I+L211D mutations, F46 variant having S3T+V4I+S153E+A188P+V193M+V199I or combinations thereof having a keratinase/caseinase activity ratio of less than about 0.80.

2. The detergent of claim 1 wherein said protease has a KC ratio of less than about 0.70.

3. The detergent of claim 1 wherein said ratio is from about 0.2 to about 0.65.

4. The detergent of claim 1 wherein said protease has a proteolytic activity of from about 100 PU/g to about 7500 PU/g.

5. The detergent of claim 1 wherein said protease is mutant BacillUs lantus DSM 5483 variant F49 having the following mutations: S3T +V4I +A188P+V193M+V199I+L211D.

6. A detergent composition for washing fabrics composed of proteinogenic fibers comprising a proteolytically active amount of a *Bacillus lentus* protease selected from the group consisting of F49 variant having S3T+V4I+A188P+V193M+V199I+L211D mutations, F46 variant having 3ST+V4I+S154E+A188P+V193M+V199I or combination thereof having a keratinase/caseinase activity ratio of less than about 0.80 and a nonionic surfactant selected from the group consisting of a fatty alkyl polyglycoside, a fatty alkyl polyalkoxylate, a fatty acid polyhydroxyamide, an ethoxylated fatty alkylamine, a propoxylated fatty alkylamine, an ethoxylated vicinal diol, a propoxylated vicinal diol, an ethoxylated fatty acid alkyl ester, a propoxylated fatty acid alkyl ester, an ethoxylated fatty acid amide, a propoxylated fatty acid amide, and mixtures thereof.

7. The detergent of claim 6 wherein said nonionic surfactant is present in an amount of from about 2% to about 25% by weight.

8. The detergent of claim 6 further comprising an anionic surfactant selected from the group consisting of a fatty alkyl sulfate, a fatty alkyl ether sulfate, a sulfofatty acid ester, a sulfofatty acid disalt, and combinations thereof.

9. A detergent composition for washing fabrics composed of proteinogenic fibers comprising a proteolytically active amount of a *Bacillus lentus* protease selected from the group consisting of F49 variant having S3T+V4I+A188P+V193M+V199I+L211D, F46 variant having 3ST+V4I+S154E+A188P+V193M+V199I mutations and combinations thereof having a keratinase/caseinase activity ratio of less than about 0.80 and an anionic surfactant selected from the group consisting of a fatty alkyl sulfate, a fatty alkyl ether sulfate, a sulfofatty acid ester, a sulfofatty acid disalt, and combinations thereof.

10. The detergent of claim 6 wherein said anionic surfactant is present in an amount of from about 2% to about 25% by weight.

11. The detergent of claim 9 wherein said anionic surfactant is selected from the group consisting of an alkyl sulfate, an alkenyl sulfate, an alkyl ether sulfate, an alkenyl ether sulfate in wherein the alkyl or alkenyl group contains from about 8 to about 22 carbon atoms.

12. The detergent of claim 11 wherein said alkyl or alkenyl group contains from about 12 to about 18 carbon atoms.

13. The detergent of claim 1 further comprising a builder selcted from the group consisting of an alkali metal alumosilicate, a crystalline alkali metal silicate with a modulus above 1, a monomeric polycarboxylate, a polymeric polycarboxylate and mixtures thereof.

14. The detergent of claim 13 wherein said builder is present in an amount of from about 2.5% to about 60% by weight.

15. A detergent composition for washing fabrics composed of proteinogenic fibers comprising from about 20% to about 55% by weight of an inorganic builder; up to about 15% by weight of a water-soluble organic builder; from about 2.5% to about 20% by weight of an anionic surfactant; from about 1% to about 20% by weight of a nonionic surfactant; up to about 25% by weight of a bleaching agent; up to about 8% by weight of a bleach activator; up to about 20% by weight of an inorganic salt; from about 0.4% to about 1.2% by weight of a lipase, cutinase, amylase, cellulase, pullulanase, oxidase or peroxidase and a proteolytically aistive amount of a Bacillus lentus protease selected from the group consisting of F49 variant having S3T+V4I+A188P+V193M+V199I+L211D mutations, F46 variant having S3T+V4I+S154E+A188P+V193M+V199I mutations, or combinations thereof having a keratinase/caseinase activity ratio of less than about 0.80.

16. The detergent of claim 15 wherein the amount of said organic builder is from about 2% to about 12% by weight; the amount of said bleaching agent is from about 1% to about 15% by weight; the amount of said bleach activator is from about 0.5% to about 6% by weight; the amount of said inorganic salt is from about 0.1% to about 15% by weight; the amount of said lipase, cutinase, amylase, cellulase, pullulanase, oxidase or peroxidase is from about 0.4% to about 1.2% by weight.

17. The detergent of claim 16 wherein said inorganic salt is an alkali metal carbonate, an alkali metal hydrogen carbonate, or an alkali metal sulfate.

18. A detergent composition for washing fabrics composed of proteinogenic fibers comprising from about 20% to about 55% by weight of an inorganic builder; up to about 15% by weight of a water-soluble organic builder; up to about 15% by weight of an anionic surfactant; from about 4% to about 24% by weight of a nonionic surfactant; up to about 65% by weight of an inorganic salt; and a proteolytically active amount of a Bacillus lentus protease selected from the group consisting of F49 variant having S3T+V4I+A188P+V193M+V199I+L211D mutation, F46 having S3T+V4I+S154E+A188P+V193M+V199I mutations or combinations thereof having a keratinase/caseinase activity ratio of less than about 0.80.

19. The detergent of claim 18 wherein the amount of said organic builder is from about 2% to about 12% by weight; the amount of said anionic surfactant is from about 1% to about 10% by weight; the amount of said inorganic salt is from about 1% to about 30% by weight.

20. A composition comprising first and second mutant proteases wherein in said first mutant protease at least one of the amino acid residues at positions 99 and 154 are different from those in Bacillus lentus DSM 5483 and wherein in said second mutant protease at least the amino acid residue at position 211 is different from that in Bacillus lentus DSM 5483.

21. The composition of claim 20 wherein said first mutant protease is F46.

22. The composition of claim 20 wherein said second mutant protease is F49.

23. A detergent composition comprising at least one surfactant and at least a first and second mutant protease wherein in said first mutant protease at least one of the amino acid residues at positions 99 and 154 are different from those in Bacillus lentus DSM 5483 and wherein in said second mutant protease at least the amino acid residue at position 211 is different from that in Bacillus lentus DSM 5483.

24. A composition comprising at least one surfactant and a proteolytically active amount of first and second mutant proteases wherein in said first mutant protease at least one of the amino acid residues at positions 99 and 154 are different from those in Bacillus lentus DSM 5483 and wherein in said second mutant protease at least the amino acid residue at position 211 is different from that in Bacillus lentus DSM 5483.

25. The composition of claim 24 wherein said first mutant protease is F46 having the following mutations: S3T+V4I+S154E+A188P+V193M+V199I.

26. The composition of claim 24 wherein said second mutant protease is F49 having the following mutations: S3T+V4I+A188P+V193M+V199I+L211D.

27. A composition comprising at least one surfactant and a proteolytically active amount of first and second mutant Bacillus lentus proteases wherein each of said protease has an amino acid subsitution selected from the group consisting of R99G, R99A, R99S, S154D, S154E, L221 D, L211 E, and a combination thereof.

* * * * *